United States Patent
Nukui et al.

(10) Patent No.: US 8,433,031 B2
(45) Date of Patent: Apr. 30, 2013

(54) X-RAY CT APPARATUS

(75) Inventors: Masatake Nukui, Tokyo (JP); Hirofumi Yanagita, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 100 days.

(21) Appl. No.: 13/188,305

(22) Filed: Jul. 21, 2011

(65) Prior Publication Data

US 2012/0020451 A1 Jan. 26, 2012
US 2012/0213324 A9 Aug. 23, 2012

(30) Foreign Application Priority Data

Jul. 22, 2010 (JP) .................. 2010-164681

(51) Int. Cl.
*A61B 6/00* (2006.01)
(52) U.S. Cl.
USPC .................. 378/17; 378/4; 382/131
(58) Field of Classification Search ........ 378/4, 17, 378/20; 382/131
See application file for complete search history.

(56) References Cited

U.S. PATENT DOCUMENTS

| 4,624,007 | A * | 11/1986 | Muranushi ................. 378/4 |
| 6,322,248 | B1 | 11/2001 | Yanagita et al. |
| 6,751,283 | B2 * | 6/2004 | van de Haar ............... 378/17 |
| 6,904,117 | B2 * | 6/2005 | Hein et al. .................. 378/4 |
| 6,937,697 | B2 | 8/2005 | Nishide et al. |
| 7,336,759 | B2 | 2/2008 | Nukui |
| 2007/0036263 | A1 | 2/2007 | Nishide et al. |
| 2007/0053478 | A1 * | 3/2007 | Tsuyuki et al. ............... 378/4 |
| 2011/0033023 | A1 * | 2/2011 | Cao ........................... 378/4 |

FOREIGN PATENT DOCUMENTS

| JP | 2000254117 | 9/2000 |
| JP | 2005-296469 | 10/2005 |

OTHER PUBLICATIONS

Japanese Notice of Reasons for Rejection; Patent Application No. 2010-164681; dated Jun. 18, 2012; pp. 4.

* cited by examiner

*Primary Examiner* — Alexander H Taningco
(74) *Attorney, Agent, or Firm* — Armstrong Teasdale LLP

(57) ABSTRACT

An X-ray CT apparatus includes a first setting device configured to set on a scout image of a subject, a reconstruction range of a tilt image based on a desired tilt angle such that the tilt image includes a region of interest of the subject, a second setting device configured to set on the scout image a range as a scan range for a non-tilt scan, the range being placed on an inner side of a scan range necessary to reconstruct the tilt image with respect to all scan spaces in the reconstruction range, wherein the range includes the region of interest, a scan execution device configured to execute the non-tilt scan on the scan range, and a reconstruction device configured to reconstruct the tilt image including at least the region of interest with respect to the reconstruction range based on projection data acquired during the non-tilt scan.

20 Claims, 16 Drawing Sheets

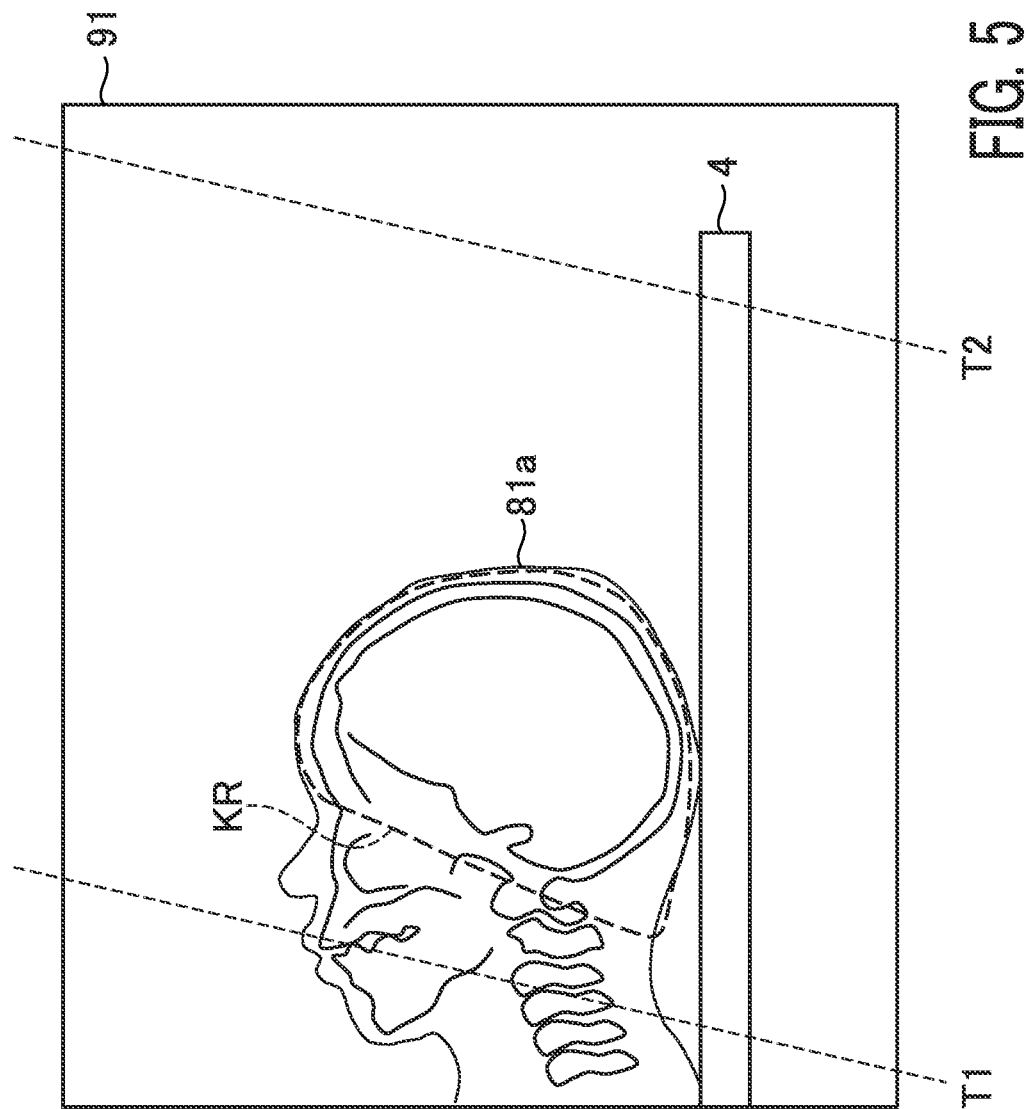
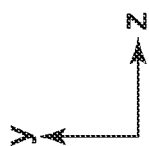

X-RAY CT APPARATUS

CROSS REFERENCE TO RELATED APPLICATIONS

This application claims the benefit of Japanese Patent Application No. 2010-164681 filed Jul. 22, 2010, which is hereby incorporated by reference in its entirety.

BACKGROUND OF THE INVENTION

The embodiments described herein relate to an X-ray CT (Computed Tomography) apparatus for reconstructing a tilt image.

As one of the imaging methods using an X-ray CT apparatus, there has conventionally been known a method for performing a scan with a gantry being tilted by its tilt mechanism thereby to obtain a tilt image whose slice plane is being tilted at a predetermined tilt angle.

To scan a head portion of a subject for example, in such a manner that a tilt image suitable for diagnosis is obtained, a gantry is tilted to perform a scan in such a manner that a scan plane matches with a reference line such as an OM line (a straight line connecting the tail of the eye and the lughole) or the like by a projector of the gantry.

Providing the gantry with the tilt mechanism, however, has the following drawbacks. For example, extra space is required in a tilting direction to enable the tilting of the gantry, and space saving is not achieved. Further, for example, the width in a z direction of the gantry tends to increase with a detector's multirowing. Therefore, a scanning table and the gantry may interfere with each other, and the design is changed as needed. For example, the tilt mechanism of the gantry is complex in structure and is rigidly built for the enhancement of its rigidity in order to make it possible to stably support a heavy casing.

Accordingly, an X-ray CT apparatus which reconstructs a tilt image, based on projection data obtained by a non-tilt scan without providing the gantry with the tilt mechanism, is also considered.

Such an X-ray CT apparatus performs such imaging as shown in the following, for example.

FIG. 16 is a diagram for explaining a general scan range setting method at the acquisition of a tilt image by a non-tilt scan.

As shown in FIG. 16, an operator first sets a tilt image reconstruction range TR0 corresponding to a conventional tilt scan range on a scout image 92 of a subject 8 in its lateral direction. The X-ray CT apparatus sets scan conditions for scanning the space of the set tilt image reconstruction range TR0 and executes a non-tilt scan in response to instructions for the start of imaging. After the completion of the non-tilt scan, the X-ray CT apparatus reconstructs the tilt image in the tilt image reconstruction range, based on acquired projection data.

Here, the X-ray CT apparatus sets scan conditions so as to be able to scan all spaces included in the tilt image reconstruction range TR0, of a scannable space defined by a scan field of view SFOV in normal times. Namely, when viewed on the scout image 92 in the lateral direction, the X-ray CT apparatus sets a range SR0 in the z direction, of an area inclusive of the tilt image reconstruction range TR0 of an area WS corresponding to the scannable space, as a scan range for a non-tilt scan. This is done to acquire a tilt image of a region of interest KR0 even though a region of interest KR0 exists in any position in the tile image reconstruction range TR0.

In fact, however, the tilt image is not required over all the spaces in the tilt image reconstruction range TR0. The tilt image may be obtained only with respect to a spatial portion corresponding to part thereof, in which the region of interest KR0 exists. Therefore, in such a scan range setting method as described above, ranges F1 and F2 unnecessary for the image reconstruction are contained in the scan range SR0, and useless exposure to the subject increases.

In view of the foregoing, there has been desired an X-ray CT apparatus capable of obtaining a tilt image of a region of interest at low exposure without using a tilt mechanism of a gantry.

SUMMARY OF THE INVENTION

A first aspect provides an X-ray CT apparatus including a first setting device for setting on a scout image of a subject in a lateral direction thereof, a desired reconstruction range of a tilt image based on a desired tilt angle so as to include a region of interest of the subject; a second setting device for setting on the scout image, a range which is placed on the inner side of a scan range necessary to reconstruct the tilt image with respect to all scan spaces in the reconstruction range set by the first setting device and includes the region of interest, as a scan range for a non-tilt scan; a scan execution device for executing a non-tilt scan on the scan range set by the second setting device; and a reconstruction device for reconstructing the tilt image including at least the region of interest with respect to the reconstruction range set by the first setting device, based on projection data acquired by execution of the non-tilt scan.

Here, the term "scan range necessary to reconstruct the tilt image with respect to the all the scan spaces in the reconstruction range set by the first setting device" can also be referred to as a range lying on the inner side of a range occupied in the direction of a body axis of the subject by an area in the reconstruction range set by the first setting device, of an area on a scout image corresponding to a scannable space defined by a scan field of view (SFOV). Incidentally, the term "scan field of view (SFOV)" is geometrically determined by a circular orbit of rotation of an X-ray source installed in a gantry, and a fan angle of a fan beam radiated from the X-ray source and corresponds to a circular area centered on the center of rotation of the gantry.

A second aspect provides an X-ray CT apparatus according to the first aspect, wherein the first setting device sets the reconstruction range according to an operation of an operator.

A third aspect provides an X-ray CT apparatus according to the first aspect, wherein the first setting device includes first analyzing device for analyzing the scout image, first presenting device for presenting each reconstruction range candidate, based on the result of analysis, and first control device for controlling the reconstruction range candidate according to the operation of the operator to set the reconstruction range.

A fourth aspect provides an X-ray CT apparatus according to the third aspect, wherein the first analyzing device detects the region of interest, based on the magnitudes of pixel values in the scout image, and wherein the first presenting device presents reconstruction range candidates that interpose the detected region of interest therebetween.

A fifth aspect provides an X-ray CT apparatus according to any one of the second through fourth aspects, wherein the second setting device sets a scan range for the non-tilt scan according to the operation of the operator.

A sixth aspect provides an X-ray CT apparatus according to the fifth aspect, wherein the second setting device includes second analyzing device for analyzing an image in the reconstruction range of the scout image, second presenting device for presenting each scan range candidate, based on the result of analysis, and second control device for controlling the scan range candidate according to the operation of the operator to set the scan range.

A seventh aspect provides an X-ray CT apparatus according to the sixth aspect, wherein the second analyzing device detects a range occupied in the direction of a body axis of the subject by the region of interest, based on the magnitudes of pixel values lying in the reconstruction range at the scout image, and wherein the second presenting device presents, as a scan range candidate, substantially the same range as the detected range.

An eighth aspect provides an X-ray CT apparatus according to any one of the first through seventh aspects, wherein the reconstruction device reconstructs a plurality of tilt images different in the size of a reconstruction plane.

A ninth aspect provides an X-ray CT apparatus according to any one of the first through eighth aspects, wherein the region of interest includes a skull or a brain.

A tenth aspect provides an X-ray CT apparatus according to any one of the first through eighth aspects, wherein the region of interest includes cervical spines.

According to the above aspects, a region excluding a region of interest can be eliminated from a scan range even within a set tilt image reconstruction range. A tilt image of the region of interest can be acquired at low exposure without using a tilt mechanism of a gantry.

BRIEF DESCRIPTION OF THE DRAWINGS

FIG. 5 is a diagram illustrating an input screen for a tilt image reconstruction range.

DETAILED DESCRIPTION OF THE INVENTION

Embodiments of the invention will be explained below.
First Embodiment
FIG. 1 is a diagram schematically showing the configuration of an X-ray CT apparatus according to a first embodiment.

Figure 1:
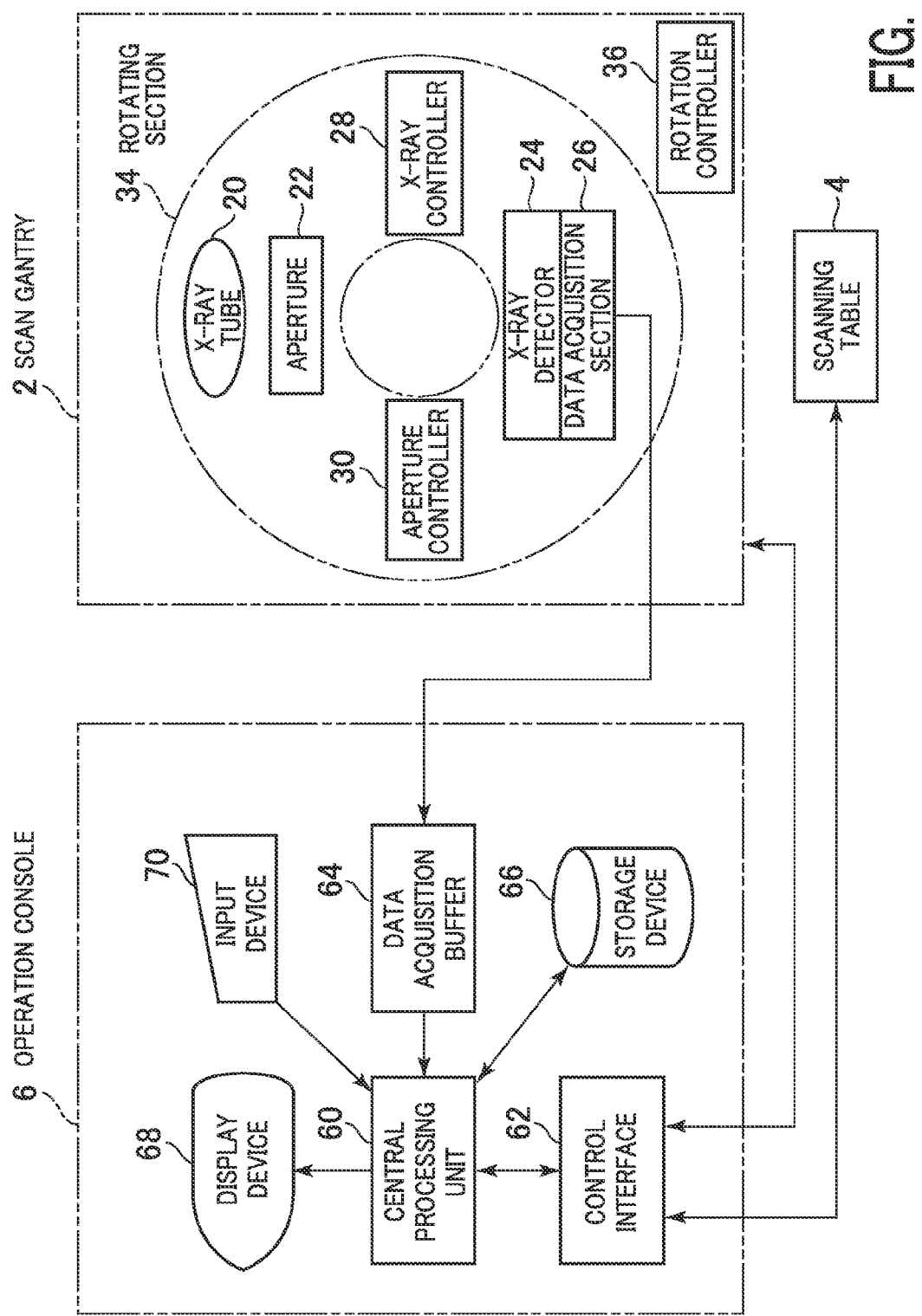
FIG. 1 is a diagram schematically showing a configuration of an X-ray CT apparatus according to a first embodiment.

As shown in FIG. 1, the present X-ray CT apparatus is equipped with a gantry 2, a scanning table 4 and an operation console 6. The gantry 2 has an X-ray tube 20. An X-ray (not shown) irradiated from the X-ray tube 20 is shaped to assume an X-ray beam such as a sectorial fan-beam, a cone beam or the like by device of an aperture 22 and applied to an X-ray detector 24.

The X-ray detector 24 has a plurality of two-dimensionally arranged X-ray detecting elements in the direction (channel direction) of expansion of the sectorial X-ray beam and its thickness direction (column direction).

A data acquisition section 26 is coupled to the X-ray detector 24. The data acquisition section 26 acquires data detected by the individual X-ray detecting elements of the X-ray detector 24 as projection data. The irradiation of X-rays from the X-ray tube 20 is controlled by an X-ray controller 28. Incidentally, the relationship of connection between the X-ray tube 20 and the X-ray controller 28 is omitted in the drawing.

Data about tube voltages and currents supplied to the X-ray tube 20 by the X-ray controller 28 are acquired by the data acquisition section 26. Incidentally, the relationship of connection between the X-ray controller 28 and the data acquisition section 26 is omitted in the drawing.

The aperture 22 is controlled by an aperture controller 30. Incidentally, the relationship of connection between the aperture 22 and the aperture controller 30 is omitted in the drawing.

Those from the X-ray tube 20 to the aperture controller 30 described above are mounted in a rotating section 34 of the gantry 2. The rotation of the rotating section 34 is controlled by a rotation controller 36. Incidentally, the relationship of connection between the rotating section 34 and the rotation controller 36 is omitted in the drawing.

The scanning table 4 carries an unillustrated subject in an X-ray irradiation space of the gantry 2 and carries the same out of the X-ray irradiation space.

The operation console 6 has a central processing unit 60. The central processing unit 60 is configured by, for example, a computer or the like. A control interface 62 is connected to the central processing unit 60. The gantry 2 and the scanning table 4 are connected to the control interface 62. The central processing unit 60 controls the gantry 2 and the scanning table 4 through the control interface 62.

The data acquisition section 26, the X-ray controller 28, the aperture controller 30 and the rotation controller 36 in the gantry 2 are controlled through the control interface 62. Incidentally, the individual connections between those parts and the control interface 62 are not illustrated in the drawing.

A data acquisition buffer 64 is connected to the central processing unit 60. The data acquisition section 26 of the gantry 26 is connected to the data acquisition buffer 64. Data acquired by the data acquisition section 26 are inputted to the central processing unit 60 through the data acquisition buffer 64.

The central processing unit 60 performs image reconstruction using projection data of a plurality of views acquired through the data acquisition buffer 64. A three-dimensional image reconstruction process or the like by, for example, a filtered back projection method is used in the image reconstruction. Incidentally, the central processing unit 60 also performs image reconstruction of a tilt image. The tilt image is of an image whose sliced plane is tilted from the non-tilted scan plane of the gantry 2, i.e., a plane perpendicular to the direction of a body axis of a subject 8. For example, a known MPR image reconstruction technique is used in the image reconstruction of the tilt image.

A storage device 66 is connected to the central processing unit 60. The storage device 66 stores therein various data, reconstructed images and a program or the like for implementing the function of the present X-ray CT apparatus.

A display device 68 and an input device 70 are respectively connected to the central processing unit 60. The display device 68 displays the reconstructed image and other information outputted from the central processing unit 60. The input device 70 is operated by an operator and inputs various instructions, information and the like to the central processing unit 60. The operator interactively operates the present X-ray CT apparatus by use of the display device 68 and the input device 70.

Incidentally, although the present X-ray CT apparatus is assumed to be one having no tilt mechanism of gantry 2 herein, it may have the tilt mechanism.

Figure 2:
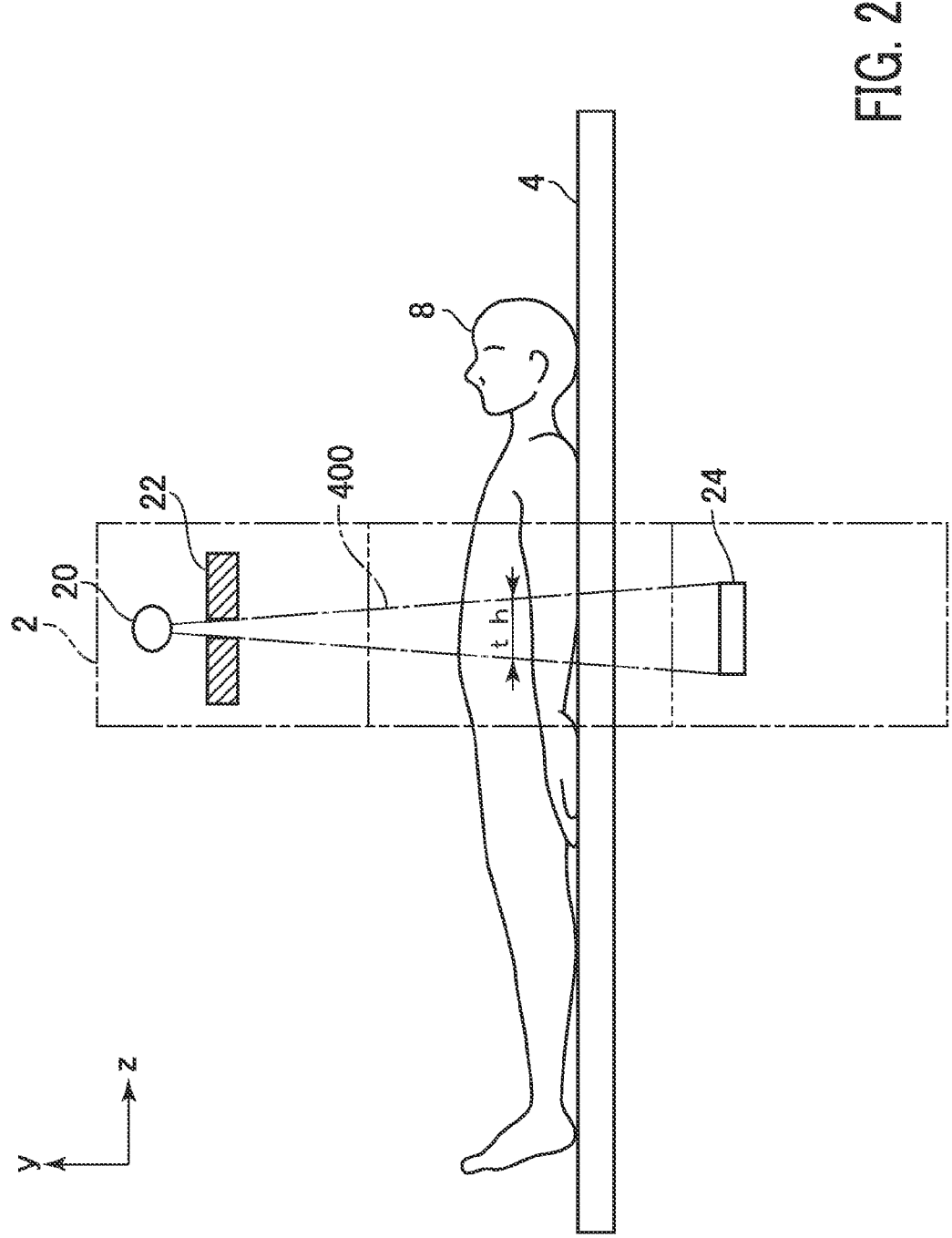
FIG. 2 is a diagram of a gantry as seen from its side surface.

FIG. 2 is a diagram of the gantry 2 as viewed from its side surface. As shown in FIG. 2, an X-ray irradiated from the X-ray tube 20 is shaped to be a fan-shaped X-ray beam 400 through the aperture 22 and applied to the X-ray detector 24. The body axis of the subject 8 is caused to intersect with the sectorial plane of such an X-ray beam 400, and the subject 8 placed on the scanning table 4 is carried in its corresponding X-ray irradiation space.

The X-ray irradiation space is shaped in space lying inside the cylindrical structure of the gantry 2. An image of the subject 8 sliced by the X-ray beam 400 is projected to the X-ray detector 24. An X-ray penetrated through the subject 8 is detected by the X-ray detector 24. The thickness the of the X-ray beam 400 applied to the subject 8 is adjusted according to the degree of opening of the aperture 22.

The X-ray tube 20, the aperture 22 and the X-ray detector 24 are rotated about the body axis of the subject 8 while maintaining the mutual relationship between them. Projection data about plural views per scan, e.g., 1000 views or so are acquired. The acquisition of the projection data is performed by a system including the X-ray detector 24, data acquisition section 26, and data acquisition buffer 64.

The central processing unit 60 performs generation or image reconstruction of a tomographic image, based on the projection data acquired by the data acquisition buffer 64.

Incidentally, the direction of the body axis of the subject 8, i.e., the direction of conveyance of the subject 8 on the scanning table 4 is assumed to be a z direction. Further, the vertical direction is assumed to be a y direction, and the horizontal direction perpendicular to the y and z directions is assumed to be an x direction.

Thus, a tilt image acquisition process according to the present embodiment will be explained.

Figure 3:
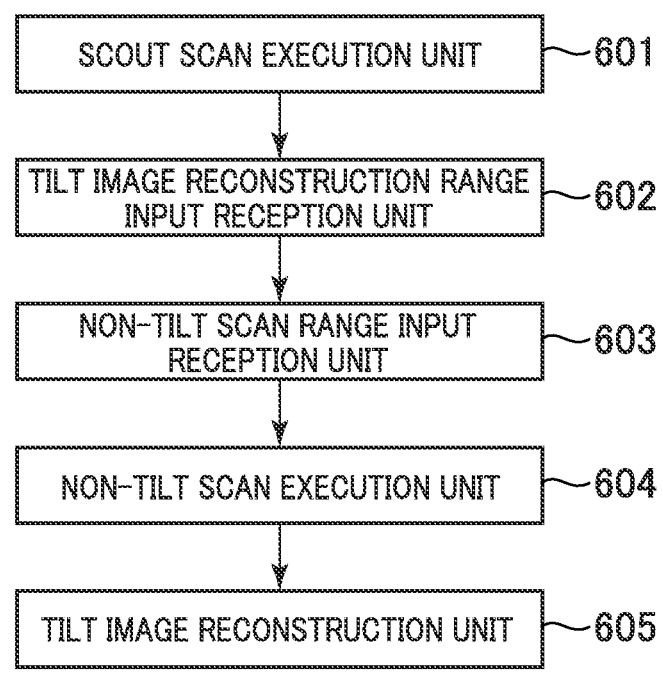
FIG. 3 is a functional block diagram of a section related to a tilt image acquisition process of the X-ray CT apparatus according to the first embodiment.

FIG. 3 is a functional block diagram of a section related to the tilt image acquisition process of the X-ray CT apparatus according to the first embodiment. FIGS. 4 through 9 are diagrams for explaining the tilt image acquisition process according to the first embodiment.

As shown in FIG. 3, the present X-ray CT apparatus has a scout scan execution unit 601, a tilt image reconstruction range input reception unit (first setting device) 602, a non-tilt scan range input reception unit (second setting device) 603, a non-tilt scan execution unit (scan execution device) 604 and a tilt image reconstruction unit (reconstruction device) 605.

The scout scan execution unit 601 controls the gantry 2 and the scanning table 4 to execute a scout scan of the subject 8 in its lateral direction. As a result, a scout image is acquired by X-ray projecting the subject 8 in its lateral direction.

One example of the scout scan in the lateral direction will now be explained. Assume that when the X-ray tube 20 is located in the top as viewed in a +y direction, the angle of rotation thereof is 0°. For example, the rotational angle of the X-ray tube 20 is first maintained at approximately 90° or 270°. In this state, an X-ray is applied while at least one of the gantry 2 and the scanning table 4 is being moved in the z direction, and the X-ray penetrated through the subject 8 is detected by the X-ray detector 24. When, however, the width of detection thereof in the z direction by the X-ray detector 24 is fully wider than the range of the scout scan in the z direction, there is no need to move the scanning table 4 or the like. Imaging is conducted while reflecting a strong-weak distribution of the penetrated X-ray onto pixel values on the basis of the data detected by the X-ray detector 24. As a result, a scout image is obtained. Incidentally, both an image itself indicative of a scout image, and image data bearing the image will be referred to as scout images herein without any distinction therebetween.

Figure 4:
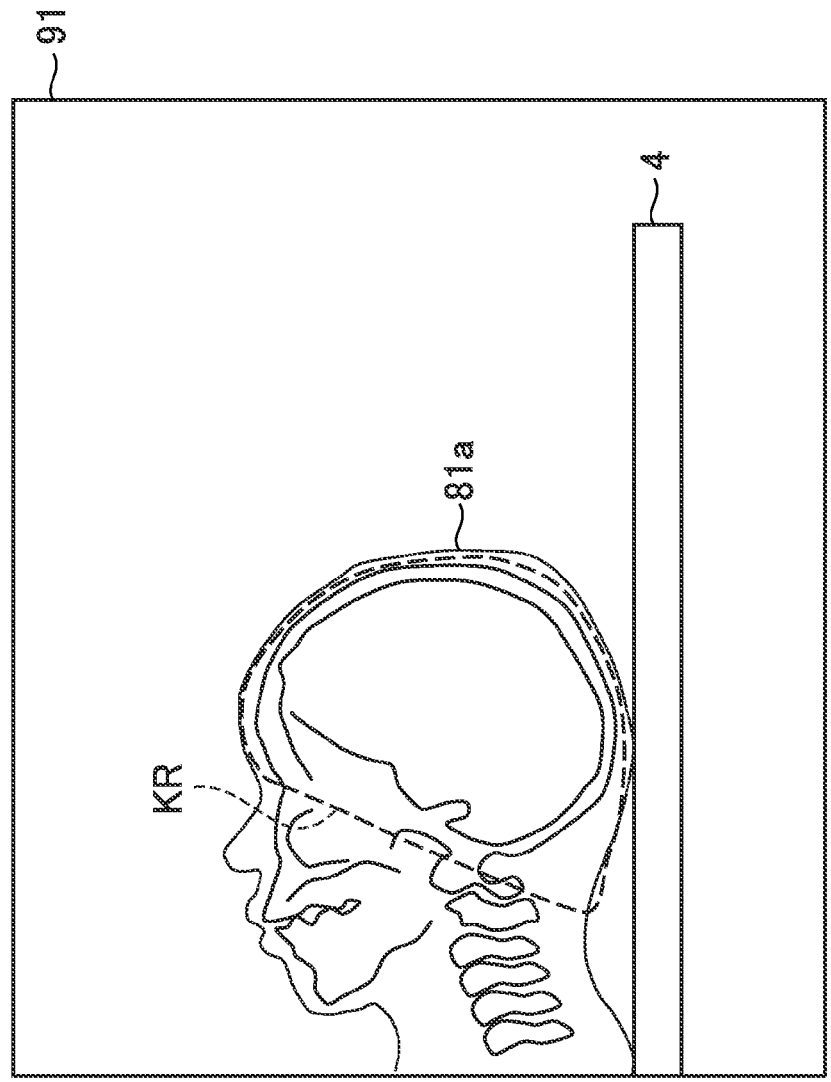
FIG. 4 is a diagram showing one example of a scout image acquired by a scout scan in a lateral direction.

The scout scan execution unit 601 performs a lateral scout scan on the head of the subject 8, for example. As a result, a scout image 91 of its head 81a such as shown in FIG. 4 is acquired. Here, a region of interest KR is a region which contains the skull and brain in the head 81a.

The tilt image reconstruction range input reception unit 602 accepts the input of a tilt angle of a tilt image to be reconstructed and a tilt image reconstruction range and sets the same. Here, the tilt angle is an angle which the slice plane of the tilt image forms with an xy plane. The tilt image reconstruction range is a range in which the tilt image based on the above tilt angle is reconstructed, and is expressed in the range in the direction of the slice axis of the tilt image.

When, for example, the scout image is acquired, the tilt image reconstruction range input reception unit 602 displays an input screen for such a tilt image reconstruction range as shown in FIG. 5. A scout image 91 is displayed in the input screen. Further, a first tilt line T1 (toward a −z direction) and a second tilt line T2 (toward a +z direction) parallel to each other are displayed on the scout image 91.

Each of the tilts of the first and second tilt lines T1 and T2 represents a tilt angle of a tilt image to be reconstructed. A range interposed between the first tilt line T1 and the second tilt line T2 represents a tilt image reconstruction range. The tilts of the first and second tilt line T1 and T2 and their positions in the z direction can be changed according to the operation of the operator while holding the relationship between the positions thereof parallel to each other. For example, a graphical user interface (GUI) or the like is used in the operation.

Figure 6:
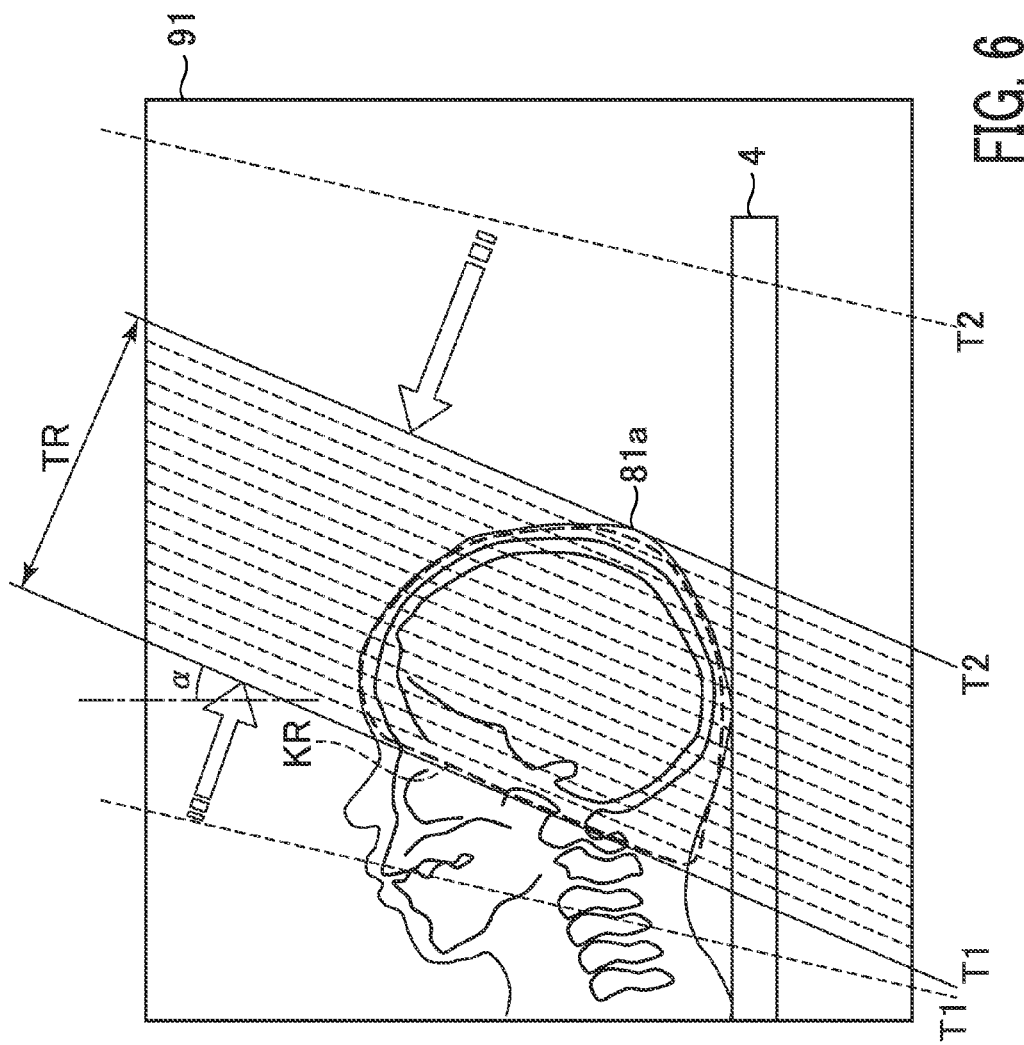
FIG. 6 is a diagram depicting the manner in which a tilt image reconstruction range is set on the input screen.

As shown in FIG. 6, the operator adjusts the tilts of the first and second tilt lines and their positions in the z direction in such a manner that they represent a desired tilt angle and a desired tilt image reconstruction range. In the present example, the desired tilt angle is a tilt angle at which the slice plane of the tilt image becomes approximately parallel to an OM line of the subject 8. The desired tilt image reconstruction range is such a tilt image reconstruction range as to catch or hold the region of interest KR therein.

After the first and second tilt lines T1 and T2 have been adjusted, the operator performs the operation of their determination. The tilt image reconstruction range input reception unit 602 sets a tilt angle α and a tilt image reconstruction range TR in response to the operation of their determination on the basis of the tilts of the first and second tilt lines T1 and T2 and their positions in the z direction at this time.

Incidentally, when the number of tilt images to be reconstructed or a slice thickness is set here, the respective positions at which the tilt images are reconstructed are represented like broken lines shown in FIG. 6.

The non-tilt scan range input unit 603 accepts the input of a scan range for a non-tilt scan and sets it. Here, the non-tilt scan is a scan to be performed without tilting the gantry 2. Namely, the non-tilt scan is a scan at which a scan plane therefor is perpendicular to the z direction.

Figure 7:
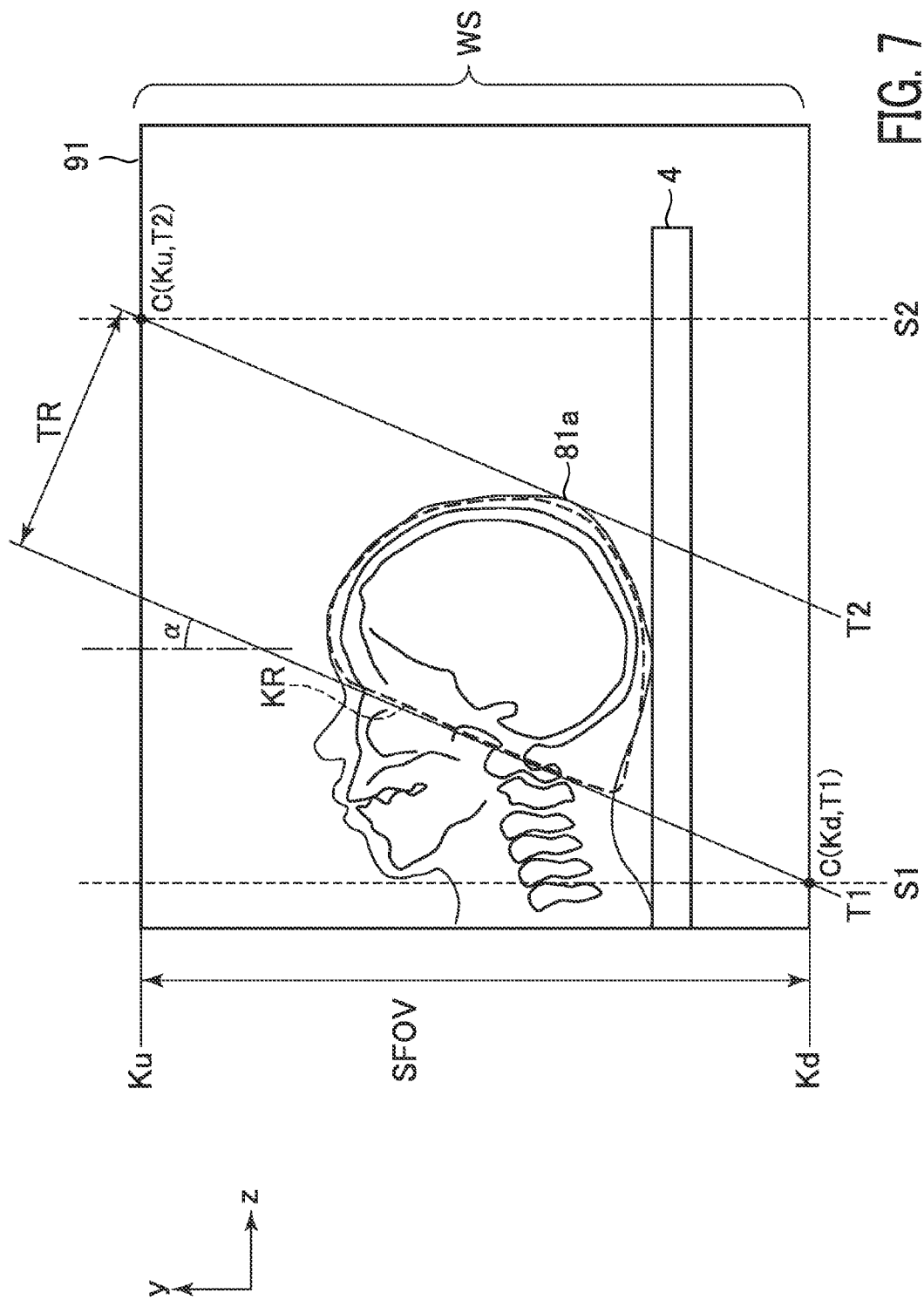
FIG. 7 is a diagram showing an input screen for a scan range of a non-tilt scan.

When, for example, the tilt angle and the tilt image reconstruction range are set, the non-tilt scan range input unit 603 displays an input screen for the scan range of a non-tile scan such as shown in FIG. 7. A scout image 91 and first and second tilt lines T1 and T2 are displayed on the input screen. Further, a first line S1 (toward a −z direction) and a second line S2 (toward a +direction) parallel to the y direction are displayed on the scout image 91.

A range interposed between the first line S1 and the second line S2 represents a scan range in the z direction, of the non-tilt scan. The positions in the z direction, of the first and second lines S1 and S2 are variable according to the operation of the operator while holding the relationship between the positions parallel to each other, of the first and second lines S1 and S2.

A description will now be given to one example of a default display of the first and second lines S1 and S2. As shown in FIG. 7, the first line S1 is displayed at such a position as to pass through a point C (Kd, T1) where a boundary line Kd lying toward a −y direction, of an area WS corresponding to a scannable space defined by an SFOV (Scan Field Of View), and the first tilt line T1 intersect. Further, the second line S2 is displayed at such a position as to pass through a point (Ku, T2) where a boundary line Kn lying toward a +y direction, of the area WS and a second tilt line T2 intersect. Such first and second lines S1 and S2 represent a scan range necessary to reconstruct each tilt image with respect to all spaces in a tilt image reconstruction range TR, of the scannable space defined by the SFOV.

Figure 8:
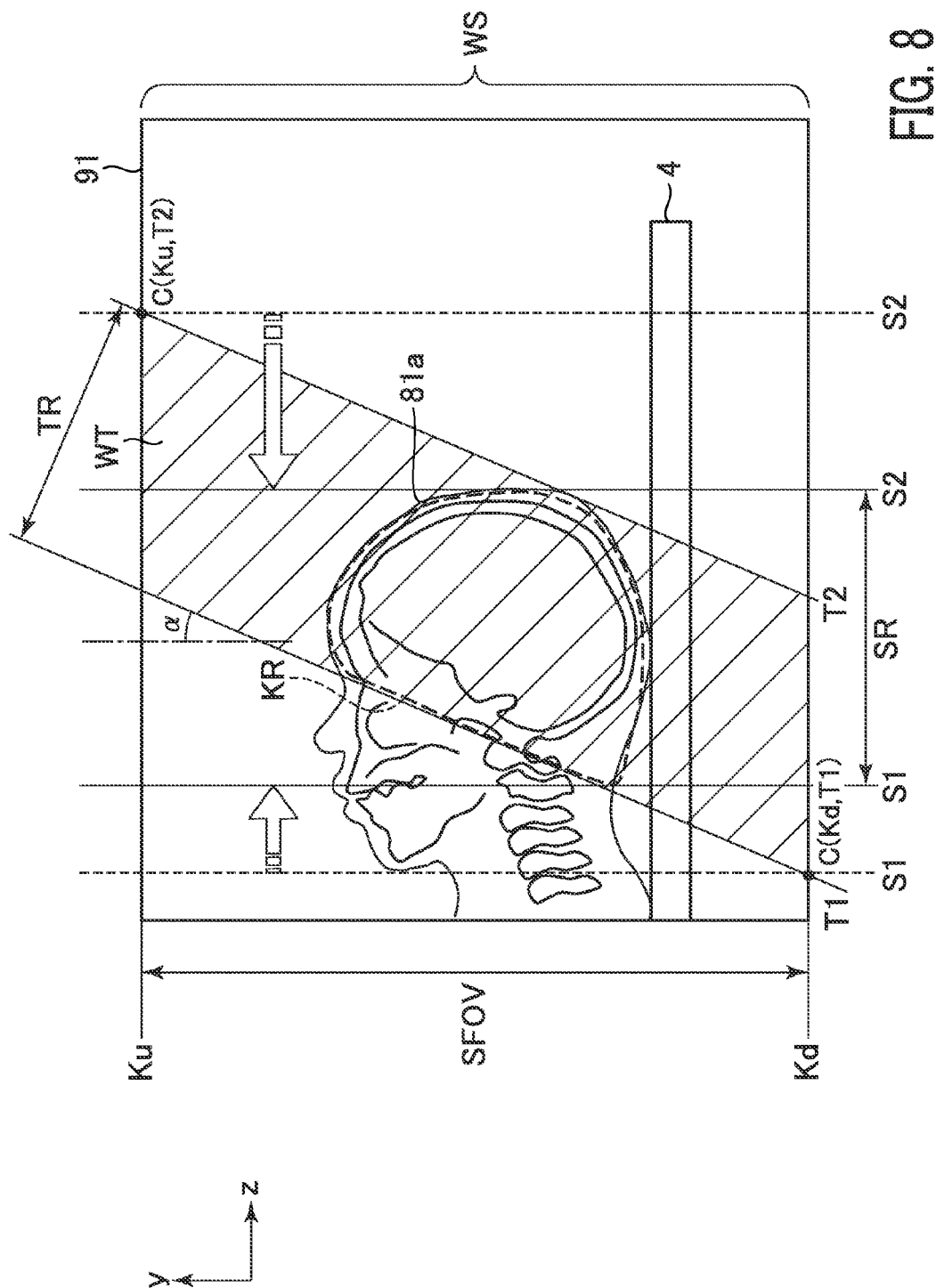
FIG. 8 is a diagram illustrating the manner in which a scan range is set on the input screen.

The operator adjusts the positions in the z direction, of the first and second lines S1 and S2 in such a manner that the first and second lines S1 and S2 represent a desired scan range as shown in FIG. 8. The desired scan range is such a scan range that unnecessary exposure to the subject 8 is normally reduced. Namely, the desired scan range is of a scan range in which a range in the z direction, of at least part of the area that needs no tilt image, of the area WT lying in the tilt image reconstruction range TR in the area WS corresponding to the scannable space defined by the SFOV is eliminated. Thus, in the present example, the desired scan range is of the range placed on the inner side of the range occupied in the z direction by the area WT in the tilt image reconstruction range TR on the scout image 91 and corresponds to the range including the region of interest KR.

After the first and second lines S1 and S2 have been adjusted, the operator performs the operation of their determination. In response to the operation of their determination, the non-tilt scan range input reception unit 603 sets a scan range SR for a non-tilt scan on the basis of the positions in the z direction, of the first and second lines S1 and S2. Incidentally, in the example shown in FIG. 8, such a scan range SR as to approximately match with the range occupied in the z direction by the region of interest KR is set.

When the scan range is set and the operator performs the operation of scan execution, the non-tilt scan execution unit 604 controls the gantry 2, the scanning table 4 and the aperture 22 and thereby executes a non-tilt scan on the set scan range SR. As a result, projection data in the scan range SR for the non-tilt scan are acquired.

The tilt image reconstruction unit 605 reconstructs a tilt image at a tilt angle α, of the region of interest KR in the tilt image reconstruction range TR, based on the acquired projection data. The position and breadth of a reconstruction plane of the tilt image assume those indicated by a plurality of thick oblique lines of FIG. 9, for example.

Figure 9:
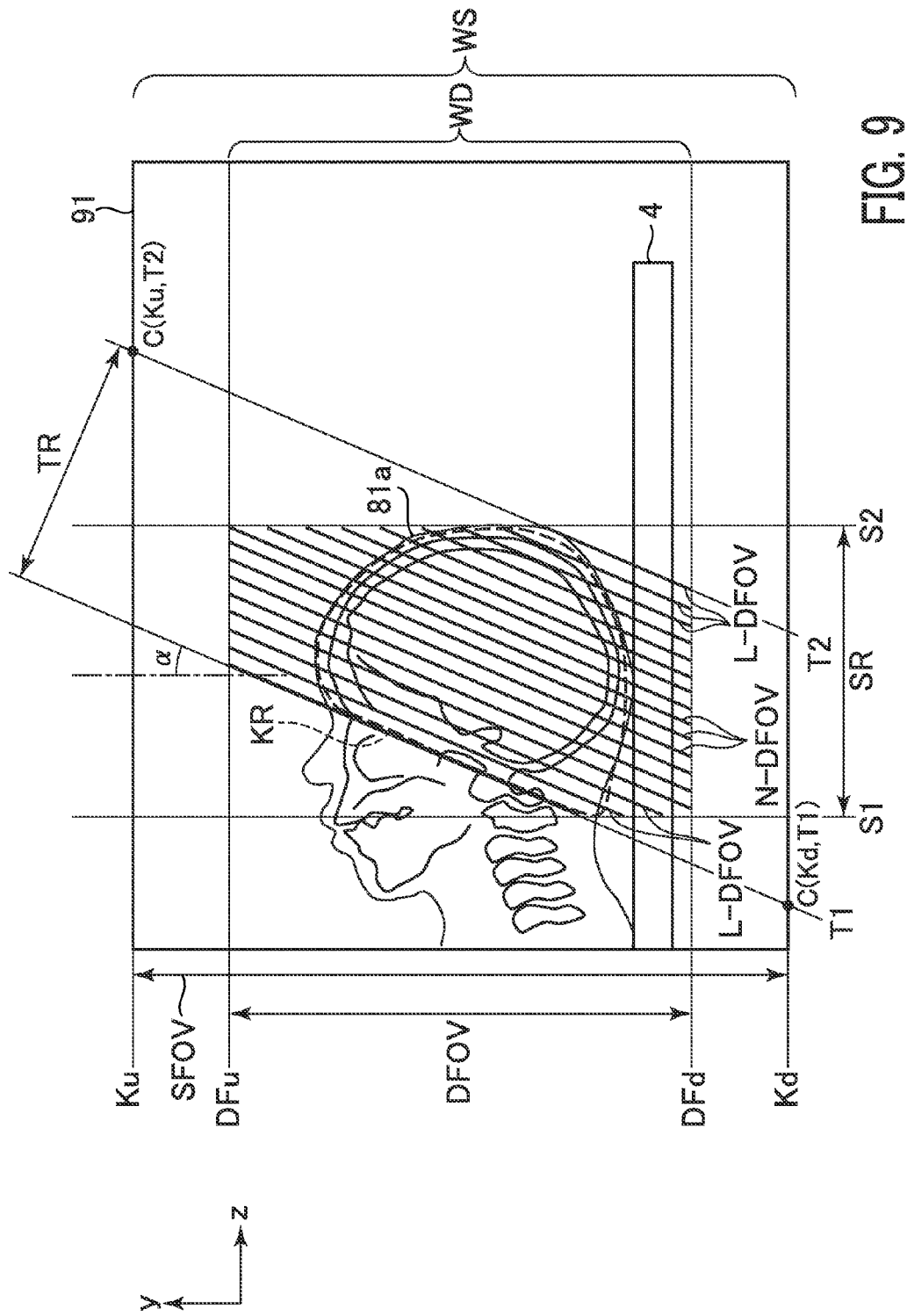
FIG. 9 is a diagram showing a reconstruction plane of a tilt image.

The range in the y direction, of the reconstruction plane of the tilt image basically coincides with a range of a reconstruction area DFOV as shown in FIG. 9. No projection data are however acquired with respect to the area out of the scan range SR in the z direction, of the area in a tilt image reconstruction range TR at an area WD (between boundary lines DFu and DFd) corresponding to a reconstruction space defined by the DFOV (Display Field Of View). Therefore, the range in the y direction, of the reconstruction plane of the tilt image results in one in which ranges (N-DFOV) coincident with the range of the DFOV, and ranges (L-DFOV) narrowed due to non-acquisition of the projection data exist in mixed form as shown in FIG. 9.

Nevertheless, the tilt image of the region of interest KR has been reconstructed without a lack in the region of interest, and no trouble occurs in the image diagnosis or the like of the region of interest KR.

In the general scan range setting method based on the conventional concept, the scan range necessary to reconstruct the tilt image with respect to all spaces in the tilt image reconstruction range TR, of the scannable space defined by the scan field of view SFOV is set. Namely, the range in the z direction between the point of intersection (Kd, T1) and the point of intersection (Ku, T2) is set as the scan range. On the other hand, in the present embodiment, the range including the region of interest KR and lying on the inner side of the range occupied in the z direction by the area WT in the set tilt image reconstruction range TR, of the area WS corresponding to the scannable space defined by the scan field of view SFOV is set as the scan range, thus resulting in the omission of extra scans.

Second Embodiment

A second embodiment is capable of analyzing a scout image to recognize a region of interest and semi-automatically setting a tilt image reconstruction range and a scan range for a non-tilt scan.

Figure 10:
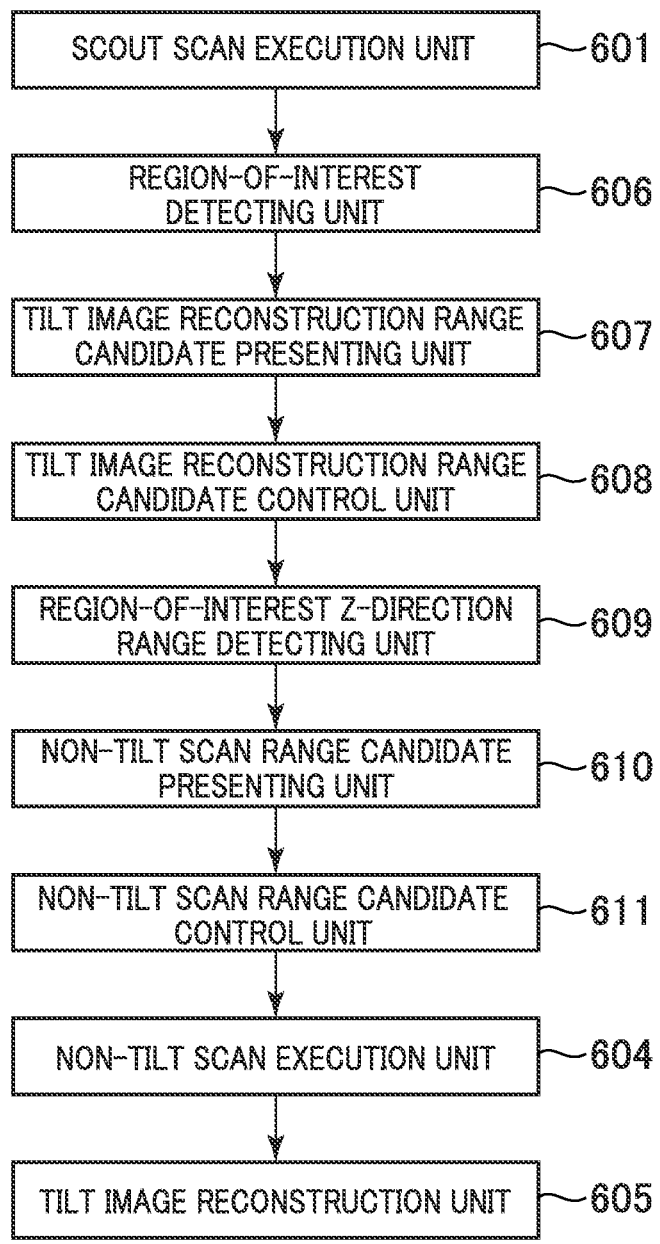
FIG. 10 is a functional block diagram of a section related to a tilt image acquisition process of an X-ray CT apparatus according to a second embodiment.

FIG. 10 is a functional block diagram of a section related to a tilt image acquisition process of an X-ray CT apparatus according to the second embodiment. FIGS. 11 through 15 are respectively diagrams for explaining the tilt image acquisition process according to the second embodiment.

As shown in FIG. 10, the present X-ray CT apparatus is equipped with a region-of-region detecting unit (first analyzing device) 606, a tilt image reconstruction range candidate presenting unit (first presenting device) 607 and a tilt image reconstruction range control unit (first control device) 608 in place of the tilt image reconstruction range input reception unit 602 with the first embodiment as a base. Further, the present X-ray CT apparatus is equipped with a region-of-interest z-direction range detecting unit (second analyzing device) 609, a non-tilt scan range candidate presenting unit (second presenting device) 610 and a non-tilt scan range candidate control unit (second control device) 611 in place of the non-tilt scan range input reception unit 603.

The region-of-interest detecting unit 606 analyzes a scout image 91 to detect a region of interest KR of a subject 8 on the scout image 91. For example, the region-of-interest detecting unit 606 detects the region of interest KR by template matching. In the preset embodiment, the region of interest KR is a region including the skull and brain of the head 81*a*.

Figure 11:
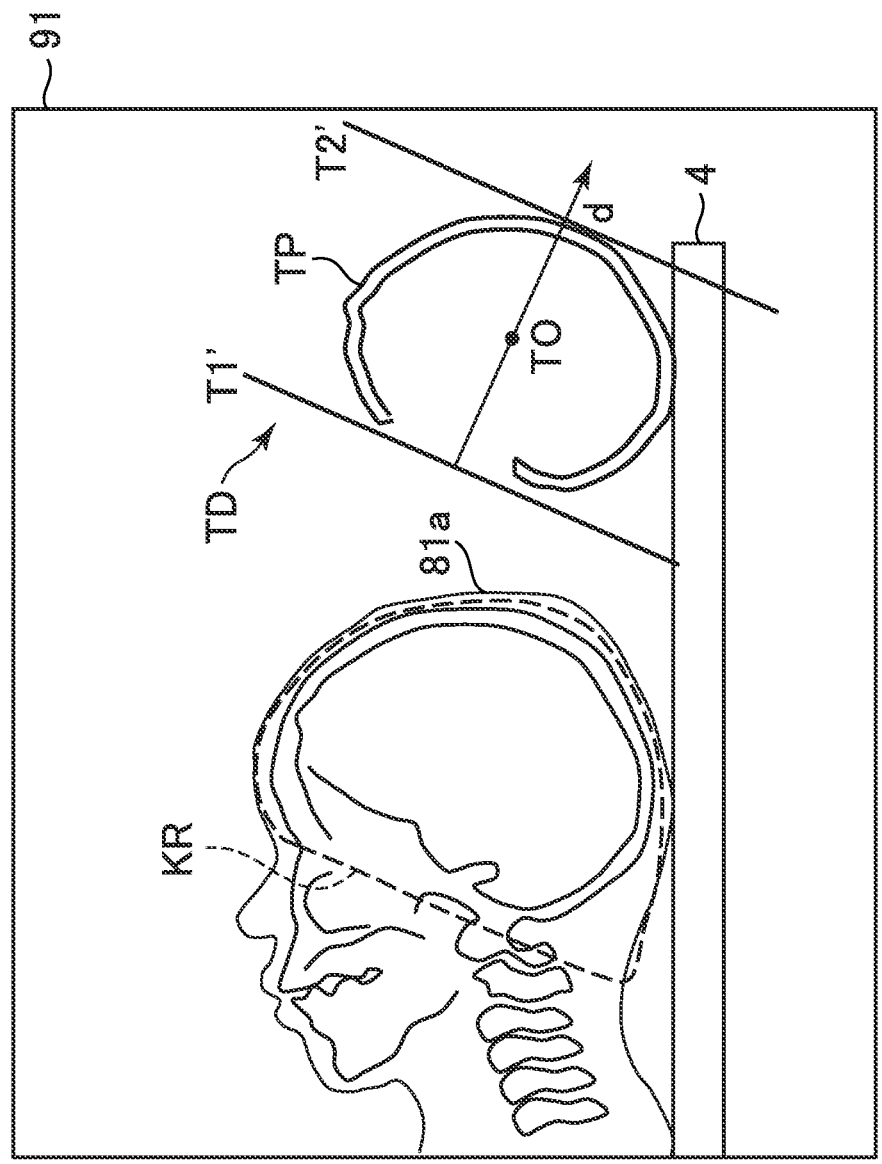
FIG. 11 is a diagram showing the manner in which a region of interest is detected by template matching on an edge image.

The region-of-interest detecting unit 606 stores therein a template TP of such a skull as shown in FIG. 11, for example. The template TP of the skull is of one obtained by simulating the skull of a head standard model. At the template TP, first and second auxiliary lines T1' and T2' which are parallel to an OM line of the head standard model and interposes the skull therebetween with a predetermined tilt, are positionally associated with the template TP. When the size and direction d of the template TP are changed centering on its center point TO, the sizes and directions of the first and second auxiliary lines T1' and T2' are also changed correspondingly at the same magnification and rotational angle.

The region-of-interest detecting unit 606 performs binarization processing on the scout image 91 using, for the threshold value, a predetermined pixel value equivalent to a bone region relatively high in density. As a result, an edge image 91' in which the edge portion of the bone region at the scout image 91 has been extracted is generated. Then, the template TP is scanned on the edge image 91' while changing the size and direction of the template TP to perform template matching, whereby the approximate position of the region of interest KR including the skull and brain is detected.

The tilt image reconstruction range candidate presenting unit 607 presents a scan range candidate for a non-tilt scan on the basis of the position of the detected region of interest KR.

Figure 12:
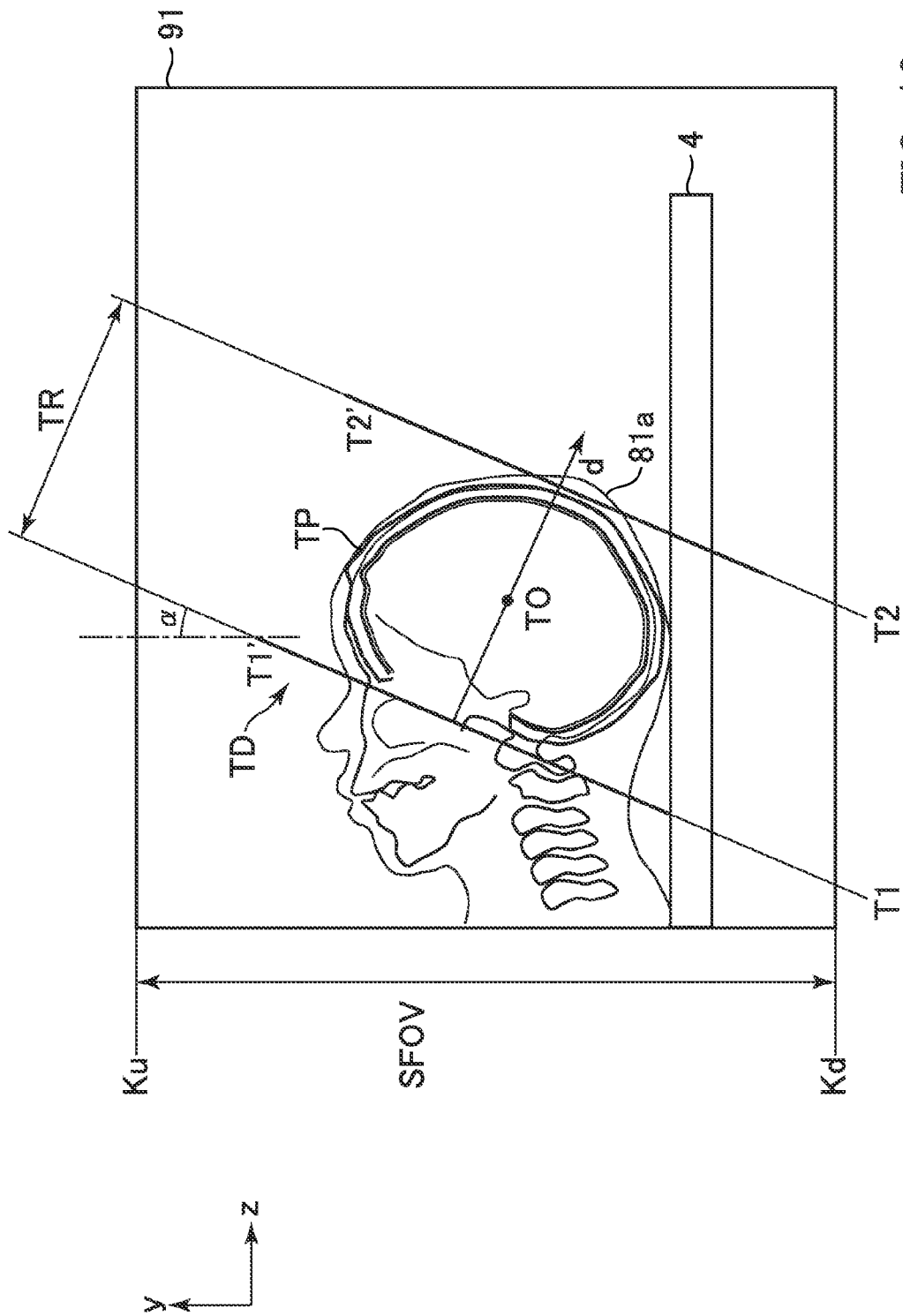
FIG. 12 is a diagram showing the manner in which tilt image reconstruction range candidates are presented based on the result of detection of a region of interest.

The tilt image reconstruction range candidate presenting unit 607 displays and presents, on the scout image 91, lines extending along the first and second auxiliary lines T1' and T2' at the time that the above template matching has been taken, as candidates for the first and second tilt lines T1 and T2 as shown in FIG. 12, for example.

The tilt image reconstruction range candidate control unit 608 accepts fine control on the candidates for the first and second tilt lines T1 and T2 according to the operation of the operator. The operator fine-controls the tilts of the first and second tilt lines T1 and T2 and their positions in the z direction as needed in such a manner that the candidates for the first and second tilt lines T1 and T2 represent a desired tilt angle and a desired tilt image reconstruction range. When the operator performs an operation for determination, the tilt image reconstruction range candidate control unit 608 sets a tilt angle α and a tilt image reconstruction range TR on the basis of the tilts of the first and second tilt lines T1 and T2 and their positions in the z direction at that time.

The region-of-interest z-direction range detecting unit 609 analyzes the scout image 91 and thereby detects a range occupied in the z direction by the region of interest KR.

Figure 13:
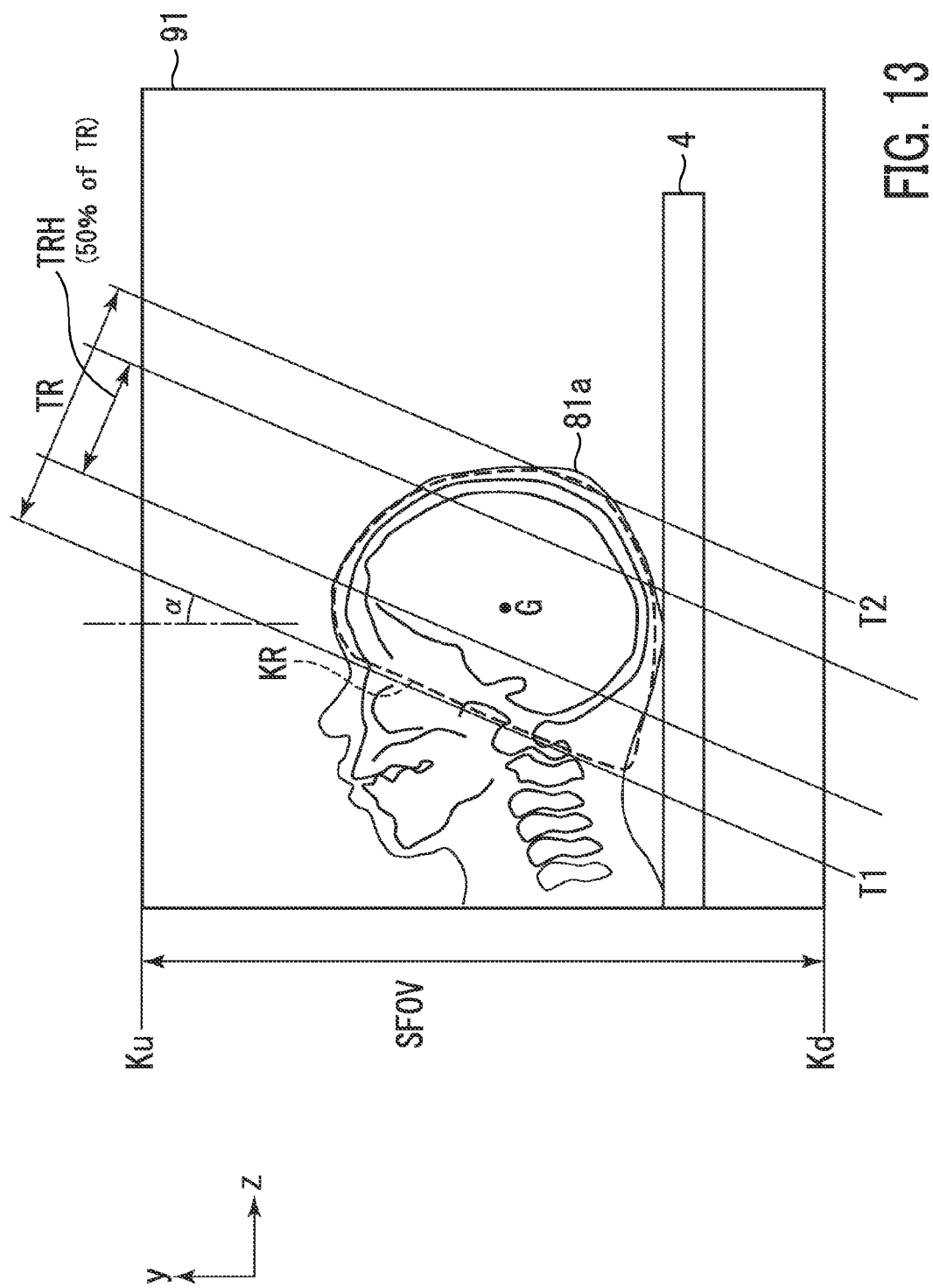
FIG. 13 is a diagram showing the manner in which the center of gravity of an image is determined in the center of the tilt image reconstruction range.

The region-of-interest z-direction range detecting unit 609 determines the center of gravity G of an image included in a range TRH of central about 50% within the tilt image reconstruction range TR in the scout image 91 as shown in FIG. 13, for example. The center of gravity G is a point corresponding to the center of a mass distribution at the time that each pixel value is assumed to be a density.

Figure 14:
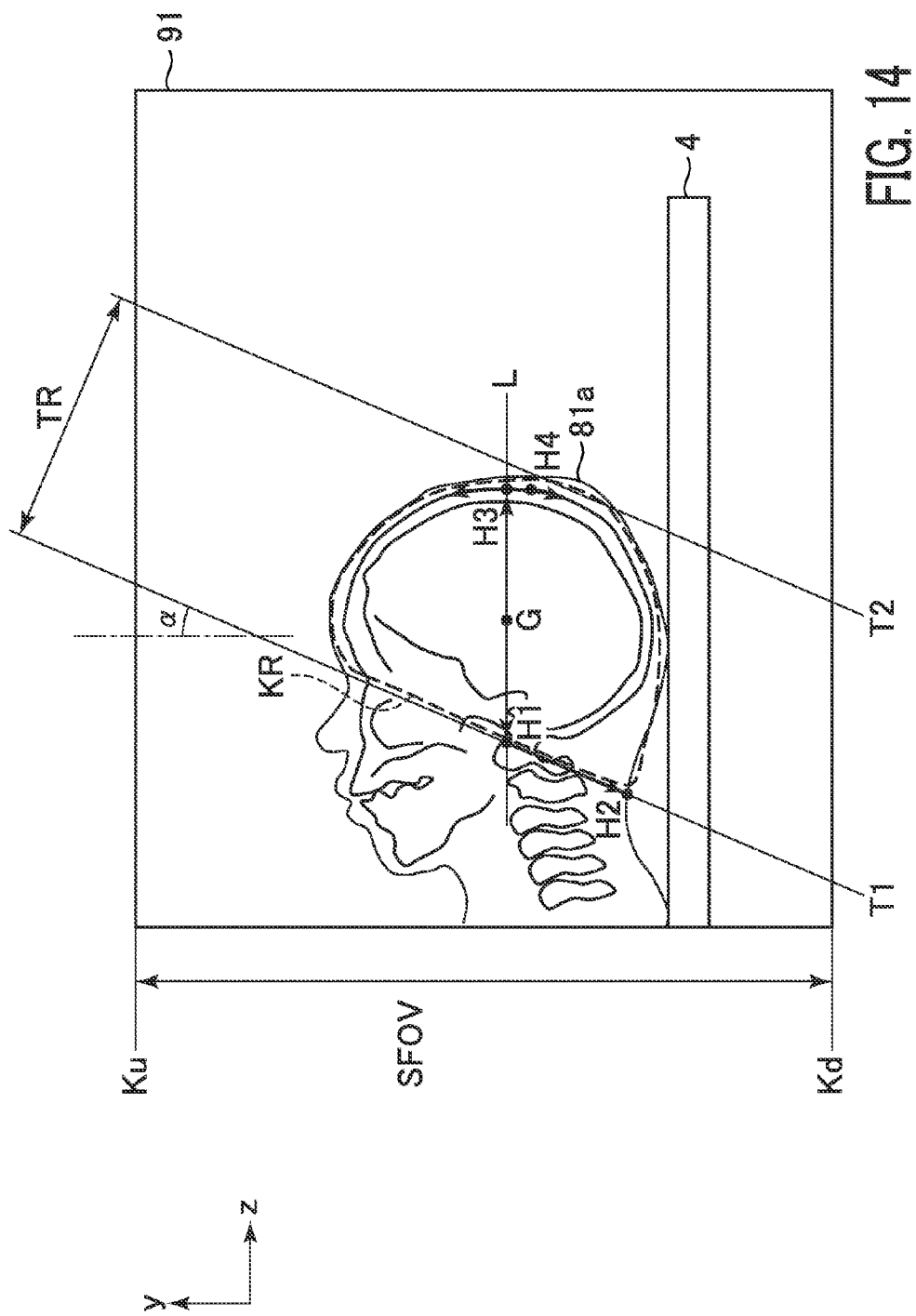
FIG. 14 is a diagram showing the manner in which a range in a z direction by the region of interest is detected with the determined center of gravity as a base point.

Then, a horizontal line L that passes through the center of gravity G and extends in the z direction is drawn as shown in FIG. 14. A point where the horizontal line L and the first tilt line T intersect, is assumed to be a point H1. Each edge is searched along the first tilt line T1 from the point H1 while seeing each pixel value on the −y direction side. A point of the position where the corresponding edge has been detected is assumed to be a point H2. Further, each edge is searched along the horizontal line L while seeing each pixel value in a +z direction. A point of the position where the corresponding edge has been detected, is assumed to be a point H3. The edge is traced in the vicinity of the point H3, and a point located the most toward the +z direction in the traced path is assumed to be a point H4. Here, the range in the z direction between the points H2 and H4 is detected as a range occupied in the z direction by the region of interest KR.

The non-tilt scan range candidate presenting unit 610 presents the same range as the range occupied in the z direction by the region of interest KR as the scan range candidate for the non-tilt scan.

Figure 15:
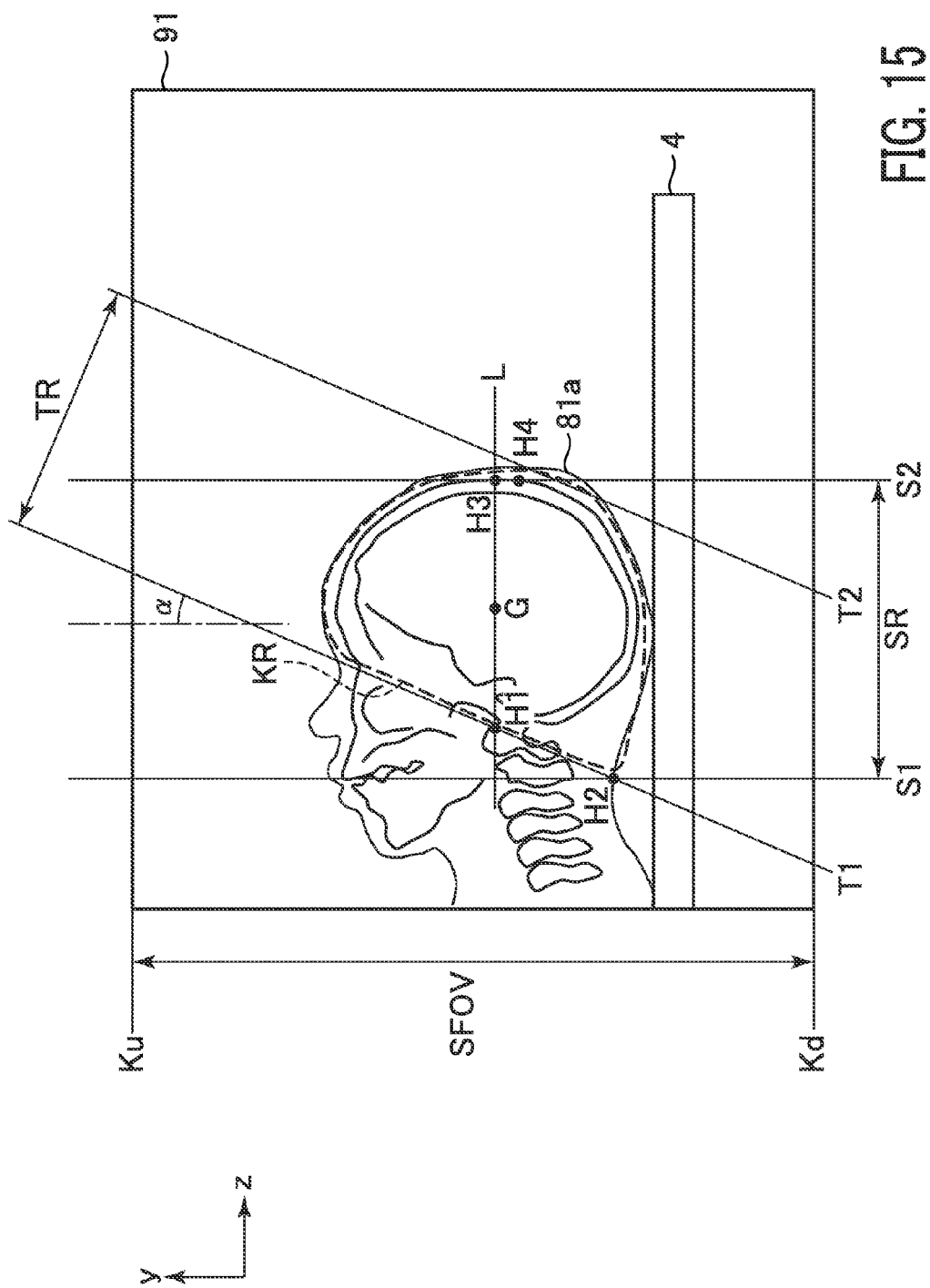
FIG. 15 is a diagram showing the manner in which scan range candidates at a non-tilt scan are presented based on the z-direction range occupied by the region of interest.
Figure 16:
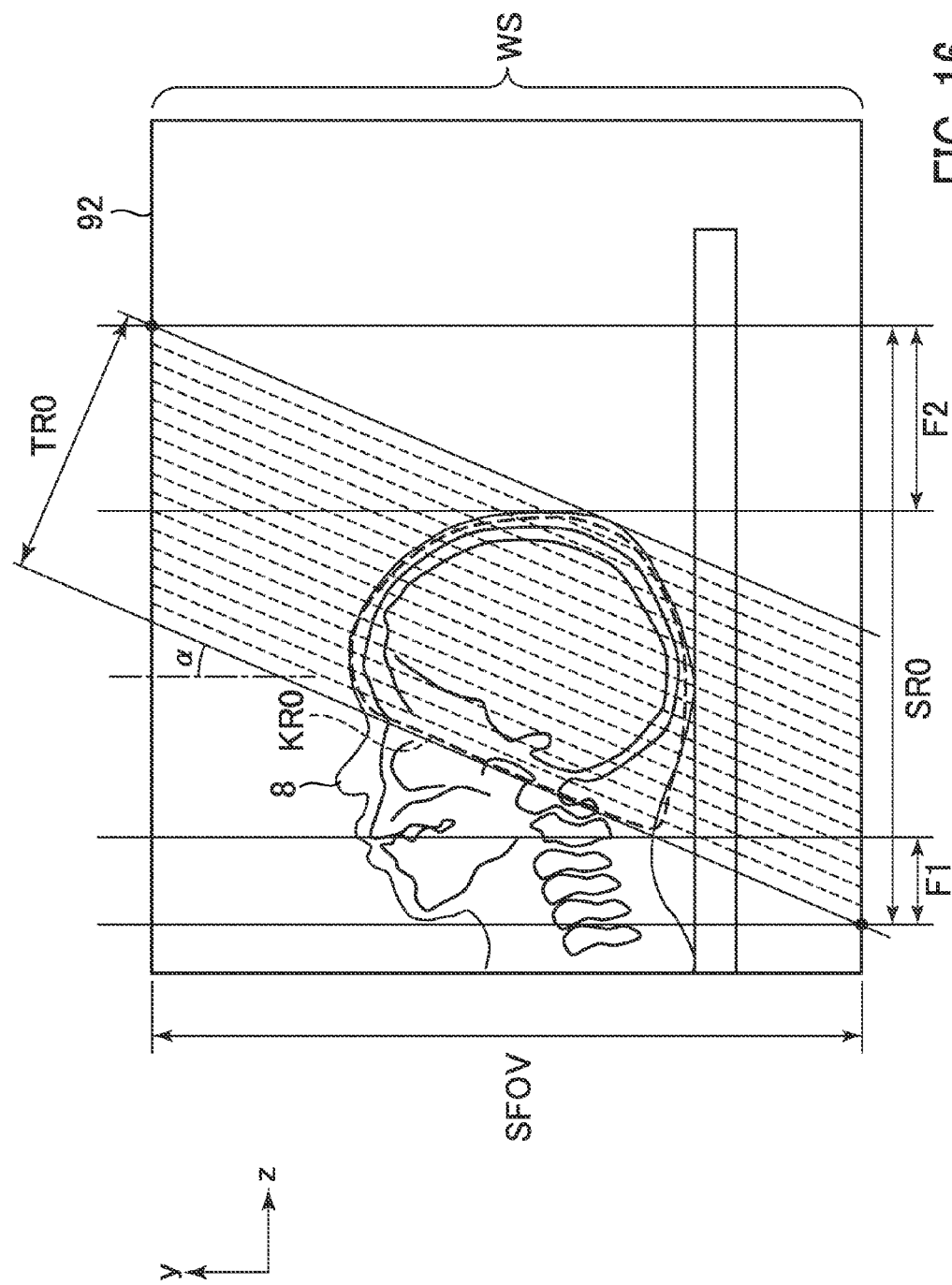
FIG. 16 is a diagram for describing a general scan range setting method at the acquisition of a tilt image by a non-tilt scan.

The non-tilt scan range candidate presenting unit 610 displays and presents a line passing through the point H2 and a line passing through the point H4 as a candidate for a first line S1 and a candidate for a second line S2, respectively, as shown in FIG. 15, for example.

The non-tilt scan range candidate control unit 611 accepts fine control on the candidates for the first and second lines S1 and S2 according to the operation of the operator. The operator fine-controls the positions in the z direction, of these lines as needed in such a manner that the candidates for the first and second lines S1 and S2 represent a desired scan range. When the operator performs an operation for determination, the non-tilt scan range candidate control unit 611 sets a scan range SR for a non-tilt scan on the basis of the positions in the z direction, of the first and second lines S1 and S2 at that time.

According to the above embodiment as described above, the region not including the region of interest KR can be eliminated from the scan range even within the set tilt image reconstruction range TR. The tilt image of the region of interest can be obtained at low exposure without using the tilt mechanism of the gantry.

According to the above embodiment as well, since no extra scan is conducted, it is also possible to achieve the shortening of a scan time and a reduction in the load on a scan system.

According to the second embodiment, since the setting of the tilt image reconstruction range and the scan range is semi-automated, a burden on the operator is lightened.

Incidentally, the embodiments of the invention are not limited to the foregoing embodiments, but may be added and modified in various ways in a range not departing from the gist of the invention.

Although the candidates are presented and semi-automated with respect to both of the tilt image reconstruction range and the scan range in the second embodiment, for example, a candidate may be presented and semi-automated only with respect to either one of these.

Although in the above embodiment, for example, the region of interest KR of the subject 8 is as the region including the skull and brain in the head, and the reference line corresponding to the slice plane of the tilt image is as the OM line, the region of interest KR and the reference line corresponding to the slice plane of the tilt image may respectively be as the cervical spine of the neck and the boundary line between the cervical spines in addition to the above.

For example, the method of analyzing the scout image, which is conducted to present the tilt image reconstruction range TR and the scan range SR in the above embodiment, is a mere one example. There are considered various methods even in addition to the above.

Although the imaging or scan conditions to be set have been described by focusing on the tilt angle α of the tilt image, the tilt image reconstruction range TR and the scan range SR for the non-tilt scan in light of the spirit of the invention in the above embodiment, for example, other imaging conditions, e.g., a slice thickness, the time taken per rotation of the gantry, an X-ray tube voltage, an X-ray tube current, a helical pitch and the like are also, of course, set as appropriate.

The invention claimed is:

1. An X-ray CT apparatus comprising:
a first setting device configured to set on a scout image of a subject in a lateral direction thereof, a desired reconstruction range of a tilt image based on a desired tilt angle such that the tilt image includes a region of interest of the subject;
a second setting device configured to set on the scout image, a scan range for a non-tilt scan, the scan range being placed on an inner side of a range necessary to reconstruct the tilt image with respect to all scan spaces in the reconstruction range set by the first setting device, wherein the scan range includes the region of interest;
a scan execution device configured to execute the non-tilt scan on the scan range set by the second setting device; and
a reconstruction device configured to reconstruct the tilt image including at least the region of interest with respect to the reconstruction range set by the first setting device based on projection data acquired by execution of the non-tilt scan.

2. The X-ray CT apparatus according to claim 1, wherein the first setting device is configured to set the reconstruction range according to an operation of an operator.

3. The X-ray CT apparatus according to claim 2, wherein the second setting device is configured to set the scan range for the non-tilt scan according to the operation of the operator.

4. The X-ray CT apparatus according to claim 3, wherein the second setting device comprises:
a second analyzing device configured to analyze an image in the reconstruction range of the scout image;
a second presenting device configured to present each scan range candidate based on the result of analysis; and
a second control device configured to control each scan range candidate according to the operation of the operator to set the scan range.

5. The X-ray CT apparatus according to claim 4,
wherein the second analyzing device is configured to detect a range occupied in a direction of a body axis of the subject by the region of interest based on magnitudes of pixel values lying in the reconstruction range at the scout image; and
wherein the second presenting device is configured to present, as a scan range candidate, substantially a same range as the detected range.

6. The X-ray CT apparatus according to claim 1, wherein the first setting device comprises:
a first analyzing device configured to analyze the scout image;
a first presenting device configured to present each reconstruction range candidate based on the result of analysis; and
a first control device configured to control each reconstruction range candidate according to the operation of the operator to set the reconstruction range.

7. The X-ray CT apparatus according to claim 6,
wherein the first analyzing device is configured to detect the region of interest based on magnitudes of pixel values in the scout image, and
wherein the first presenting device is configured to present the reconstruction range candidates that interpose the detected region of interest therebetween.

8. The X-ray CT apparatus according to claim 1, wherein the reconstruction device is configured to reconstruct a plurality of tilt images that have different sizes of a reconstruction plane.

9. The X-ray CT apparatus according to claim 1, wherein the region of interest includes a skull or a brain.

10. The X-ray CT apparatus according to claim 1, wherein the region of interest includes cervical spines.

11. A method for setting a scan range for a non-tilt scan using X-ray CT apparatus, the method comprising:
setting on a scout image of a subject in a lateral direction thereof a desired reconstruction range of a tilt image based on a desired tilt angle such that the tilt image includes a region of interest of the subject;
setting on the scout image a scan range for a non-tilt scan, the scan range placed on an inner side of a range necessary to reconstruct the tilt image with respect to all scan spaces in the reconstruction range set by the first setting device, wherein the scan range includes the region of interest;
executing the non-tilt scan on the scan range; and
reconstructing the tilt image including at least the region of interest with respect to the reconstruction range based on projection data acquired by execution of the non-tilt scan.

12. The method according to claim 11, wherein setting a desired reconstruction range comprises setting the reconstruction range according to an operation of an operator.

13. The method according to claim 12, wherein setting a scan range comprises setting the scan range for the non-tilt scan according to the operation of the operator.

14. The method according to claim 13, wherein setting a scan range comprises:
analyzing an image in the reconstruction range of the scout image;
presenting each scan range candidate based on the result of analysis; and
controlling the scan range candidates according to the operation of the operator to set the scan range.

15. The method according to claim 14, further comprising:
detecting a range occupied in a direction of a body axis of the subject by the region of interest based on magnitudes of pixel values lying in the reconstruction range at the scout image; and
presenting, as a scan range candidate, substantially a same range as the detected range.

16. The method according to claim 11, wherein setting a desired reconstruction range comprises:
analyzing the scout image;
presenting each reconstruction range candidate based on the result of analysis; and
controlling each reconstruction range candidate according to the operation of the operator to set the reconstruction range.

17. The method according to claim 16, further comprising:
detecting the region of interest based on magnitudes of pixel values in the scout image; and
presenting reconstruction range candidates that interpose the detected region of interest therebetween.

18. The method according to claim 11, wherein reconstructing the tilt image comprises reconstructing a plurality of tilt images that have different sizes of a reconstruction plane.

19. The method according to claim 11, wherein setting a desired reconstruction range comprises setting the reconstruction range such that the region of interest includes a skull or a brain.

20. The method according to claim 11, wherein setting a desired reconstruction range comprises setting the reconstruction range such that the region of interest includes cervical spines.

* * * * *